United States Patent
Von Berg et al.

(10) Patent No.: US 8,160,332 B2
(45) Date of Patent: Apr. 17, 2012

(54) MODEL-BASED CORONARY CENTERLINE LOCALIZATION

(75) Inventors: Jens Von Berg, Hamburg (DE); Bernd Hofmann, Eningen (DE); Cristian Lorenz, Hamburg (DE); Olivier Ecabert, Aachen (DE); Jochen Peters, Aachen (DE); Juergen Weese, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 462 days.

(21) Appl. No.: 12/443,490

(22) PCT Filed: Sep. 28, 2007

(86) PCT No.: PCT/IB2007/053949
§ 371 (c)(1),
(2), (4) Date: Mar. 30, 2009

(87) PCT Pub. No.: WO2008/041165
PCT Pub. Date: Apr. 10, 2008

(65) Prior Publication Data
US 2010/0046815 A1    Feb. 25, 2010

(30) Foreign Application Priority Data
Oct. 3, 2006 (EP) .................................... 06121687

(51) Int. Cl.
*G06K 9/00* (2006.01)
(52) U.S. Cl. ......................................... 382/128; 128/922
(58) Field of Classification Search .................. 128/922; 382/128, 130–132; 600/407, 414, 425–427, 600/437, 450, 481, 508
See application file for complete search history.

(56) References Cited

U.S. PATENT DOCUMENTS
6,226,418 B1 * 5/2001 Miller et al. .................. 382/294
(Continued)

FOREIGN PATENT DOCUMENTS
WO   2006036842 A2   4/2006

OTHER PUBLICATIONS
Lorenz: "A Comprehensive Shape Model of the Heart"; Medical Image Analysis, vol. 10, No. 4, 2006, pp. 657-670.
(Continued)

*Primary Examiner* — Levi Gannon

(57) ABSTRACT

The invention relates to a system (100) for registering a vessel model with an image data set based on a joined model comprising a reference object model and the vessel model, the system comprising: a placement unit (110) for placing the joined model in a space of the image data set, thereby creating a placed joined model comprising a placed reference object model and a placed vessel model; a computation unit (120) for computing a deformation field based on a landmark displacement field comprising displacements of landmarks of the placed reference object model relative to corresponding landmarks in the image data set; a transformation unit (130) for transforming the placed joined model using the deformation field, thereby creating a transformed joined model comprising a transformed reference object model and a transformed vessel model; and a registration unit (140) for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model. Hence, the system is arranged to model a vessel taking into account the localization of a vessel model relative to a reference anatomical structure described by a reference model.

11 Claims, 4 Drawing Sheets

U.S. PATENT DOCUMENTS

| | | | | |
|---|---|---|---|---|
| 6,754,374 | B1* | 6/2004 | Miller et al. | 382/128 |
| 7,200,251 | B2* | 4/2007 | Joshi et al. | 382/128 |
| 7,555,151 | B2* | 6/2009 | Comaniciu et al. | 382/128 |
| 7,764,817 | B2* | 7/2010 | Georgescu et al. | 382/128 |
| 7,876,934 | B2* | 1/2011 | Georgescu et al. | 382/128 |
| 2005/0197568 | A1 | 9/2005 | Vass et al. | |

OTHER PUBLICATIONS

Rusinkiewicz et al: "Efficient Variants of the ICP Algorithm"; Proceedings of the Third International Conference on 3-D Digital Imaging and Modeling, May 28-Jun. 1, 2001, pp. 145-152.

Beg et al: "Computational Cardiac Anatomy Using MRI"; Magnetic Resonance in Medicine (2004), vol. 52, pp. 1167-1174.

Frangi et al: "Model-Based Quantitation of 3-D Magnetic Resonance Angiographic Images"; IEEE Transactions on Medical Imaging, vol. 18, No. 10, Oct. 1999, pp. 946-956.

Frangi et al: "Three-Dimensional Model-Based Stenosis Quantification of the Carotid Arteries From Contrast-Enhanced MR Angiography"; IEEE Workshop on Mathematical Methods in Biomedical Image Analysis, IEEE 2000, pp. 110-118.

Lorenz et al: "Towards a Comprehensive Geometric Model of the Heart"; FIMH 2005, LNCS 3504, pp. 102-112.

McInerney et al: "Deformable Models in Medical Image Analysis: A Survey"; Medical Image Analysis, 1996, vol. 1 (2), pp. 91-108.

Niessen et al: "Model-Based Segmentation of Cardiac and Vascular Images"; Proceedings of the 2002 IEEE International Symposium on Biomedical Imaging, pp. 22-25.

Lorenz et al: "Modeling the Coronary Artery Tree"; Proc. of IEEE International Conference on Shape Modeling International (SMI), Genova, Italy, Jun. 6-9, 2004, pp. 354-357.

Frangi et al: "Multiscale Vessel Enhancement Filtering"; Medical Image Computing and Computer Assisted Intervention-MCCAI'98, Lecture Notes in Computer Science, vol. 1496, pp. 130-137.

von Berg et al: "Multi-Surface Cardiac Modelling, Segmentation, and Tracking": FIMH 2005, LNCS 3504, Springer-Verlag, 2005, pp. 1-11.

Lorenz et al: "Fast Automated Object Detection by Recursive Casting of Search Rays"; Cars (2005), International Congress Series 1281 (2005), pp. 230-235.

Schramm et al: "Towards Fully Automatic Object Detection and Segmentation"; Medical Imaging 2006: Image Processing, Edited by Joseph M. Reinhardt and Josien P.W. Pluim, Proc. of SPIE vol. 6144, pp. 614402-1-614402-10.

Bookstein, F.: "Principal Warps: Think-Plate Splines and the Decomposition of Deformations"; IEEE Transactions on Pattern Analysis and Machine Intelligence, vol. 11, No. 6, pp. 567-585, Jun. 1989.

Ecabert et al: "Towards Automatic Full Heart Segmentation in Computed-Tomography Images"; 32nd Conference on Computers in Cardiology, 2005, 32, pp. 223-226.

Weese et al: "Shape Constrained Deformable Models for 3D Medical Image Segmentation"; IPMI 2001, LNCS 2082, pp. 380-387, 2001.

Lorenz et al: "A Multi-Scale Line Filter With Automatic Scale Selection Based on the Hessian Matrix for Medical Image Segmentation"; Lecture Notes in Computer Science, vol. 1252, Proceedings of the First International Conference on Scale-Space Theory in Computer Vision, 1997, pp. 152-163.

Sato et al: "3D Multi-Scale Line Filter for Segmentation and Visualization of Curvilinear Structures in Medical Images"; Lecture Notes in Computer Science, vol. 1205, Conference on Computer Vision, Virtual Reality and Robotics in Medicine and Medial Robotics and Computer-Assisted Surgery, 1997, pp. 213-222.

Peters et al: "Feature Optimization Via Simulated Search for Model-Based Heart Segmentation"; Cars 2005, International Congress Series 1281 (2005), pp. 33-38.

Borgefors, G.: "Distance Transformations in Digital Images", IEEE Transactions on Pattern Analysis and Machine Intelligence, vol. 34, 1986, pp. 344-371.

* cited by examiner

MODEL-BASED CORONARY CENTERLINE LOCALIZATION

FIELD OF THE INVENTION

The invention relates to the field of medical image data segmentation and, more specifically, to segmenting vessels in medical image data.

BACKGROUND OF THE INVENTION

A model-based approach to segmentation of vascular and cardiac images is presented in an article by A. F. Frangi et al entitled "Model-Based Quantification of 3-D Magnetic Resonance Angiographic Images" in IEEE Transactions on Medical Imaging, Vol. 18, No. 10, 1999, pages 946-956, hereinafter referred to as Ref. 1. The paper describes two-step model-based vessel segmentation. First, a representation of the central vessel axis, hereinafter also referred to as the vessel centerline, is obtained. The model vessel centerline is described using a B-spline curve of degree n with s+1 control points. The model vessel centerline is adapted to the centerline of the vessel comprised in the image by minimizing an energy function, also referred to as a cost function or an objective function. The energy function comprises an external term and an internal energy term. The internal energy term comprises a stretching energy term and a bending energy term. The stretching energy term and the bending energy term define internal constraints on the deformation of the vessel centerline. The external energy term defines attraction of the vessel centerline to 3-D image features which are likely to lie on the central axis of the vessel. A vesselness filter described in an article by A. F. Frangi et al entitled "Multiscale vessel enhancement filtering", in Medical Image Computing and Computer Assisted Intervention—MICCAI'98, W. M. Wells, A. Colchester and S. L. Delp (Eds.), Lecture Notes in Computer Science, Vol. 1496—Springer Verlag, Berlin, Germany, pages 130-137, hereinafter referred to as Ref. 2, is employed.

SUMMARY OF THE INVENTION

A further improvement of the method described in Ref. 1 is possible. The prior knowledge terms in the objective function described in Ref. 1, i.e. the stretching energy term and the bending energy term, are based on shape priors, i.e. prior knowledge terms based on a prior knowledge of the vessel shape, defined by the model vessel centerline. However, the prior knowledge terms of Ref. 1 do not take into account location priors, i.e. prior knowledge terms based on a prior knowledge of the localization of the vessel, defined by the localization of the vessel centerline relative to a reference anatomical structure comprised in the image data set.

It would be advantageous to have a system for modeling a vessel taking into account the localization of a vessel model relative to a reference anatomical structure identified in the image data set.

To address this concern, in an aspect of the invention, a system for registering a vessel model with an image data set based on a joined model comprising a reference object model and the vessel model comprises:

a placement unit for placing the joined model in a space of the image data set, thereby creating a placed joined model comprising a placed reference object model and a placed vessel model;

a computation unit for computing a deformation field based on a landmark displacement field comprising displacements of landmarks of the placed reference object model relative to corresponding landmarks in the image data set;

a transformation unit for transforming the placed joined model using the deformation field, thereby creating a transformed joined model comprising a transformed reference object model and a transformed vessel model; and a registration unit for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model.

The invention describes a system for segmenting the image data set in two steps. In the first step, the placed reference object model and the placed vessel model comprised in the placed joined model are transformed by the transformation unit using the deformation field computed by the computation unit. The deformation field is determined based on displacements of landmarks of the placed reference object model relative to corresponding landmarks in the image data set. While this transformation may be sufficient for modeling the reference object in the image data set, it is likely to be just a satisfactory initialization of the placed vessel model. Thus, in the second step, the transformed vessel model is registered with the image data set based on modifying the transformed vessel model and optimizing the objective function of the modified transformed vessel model. The objective function comprises a location-prior term based on a localization of the modified vessel model relative to the transformed joined model. Hence, the system is arranged to model a vessel taking into account the localization of a vessel model relative to a reference anatomical structure described by a reference model.

In an embodiment of the system, the system further comprises an adaptation unit for adapting the placed reference object model to the image data set, thereby defining the corresponding landmarks in the image data set. The placed reference object model comprising the landmarks, e.g. defined based on a user input, is adapted to the image dataset. The landmarks of the adapted placed reference object model defines the corresponding landmarks in the image data set. Adapting the placed reference object model may significantly simplify and/or improve computing the landmark displacement field comprising displacements of landmarks of the placed reference object model relative to corresponding landmarks in the image data set.

In an embodiment of the system, the reference object model comprises a mesh comprising a plurality of vertices. The placed reference object model comprises a placed mesh. The adaptation unit adapts the placed reference object model, i.e. the placed mesh, to the image data set. There exist many useful methods for adapting a mesh to an image data set. A placed vertex of the placed mesh may be used as a landmark of the placed model and the adapted placed vertex of the adapted placed mesh may be used as the corresponding landmark. This is a convenient way of creating a large number of useful corresponding landmarks.

In an embodiment of the system, the vessel model comprises a plurality of control points for describing a vessel centerline. Such a vessel centerline may be piecewise linear or may be modeled using B-splines, for example. Using the vessel centerline described by a plurality of control points describes an important aspect of the modeled vessel and is convenient for implementing the objective function.

In an embodiment of the system, the objective function further comprises a vesselness term based on a vesselness filter for computing a measure of vesselness at a location of the vesselness filter in the space of the image data set. A suitable vesselness filter is defined, for example, in Ref. 2. The vesselness term allows the modified transformed vessel model to be attracted to a likely location of a vessel comprised in the image data set.

In an embodiment of the system, the vessel model further comprises a plurality of diameters of the vessel for describing a vessel wall. Employing the plurality of diameters as parameters of the vessel model allows for a simple determination of values of a scale parameter of the vesselness filter at a location of the vesselness filter in the space of the image data set.

In an embodiment of the system, the location-prior term depends on the transformed reference object model. The location-prior term dependent on the transformed reference object model improves guiding the registration of the transformed vessel model to the image data set by penalizing deformations of the modified transformed vessel model, which result in a localization of the modified transformed vessel model relative to the transformed reference object model very different from the localization of the transformed vessel model relative to the transformed reference object model.

In a further aspect of the invention, the system according to the invention is comprised in an image acquisition apparatus.

In a further aspect of the invention, the system according to the invention is comprised in a workstation.

In a further aspect of the invention, a method of registering a vessel model with an image data set based on a joined model comprising a reference object model and the vessel model comprises:

a placement step for placing the joined model in a space of the image data set, thereby creating a placed joined model comprising a placed reference object model and a placed vessel model;

a computation step for computing a deformation field based on a landmark displacement field comprising displacements of landmarks of the placed reference object model relative to corresponding landmarks in the image data set;

a transformation step for transforming the placed joined model using the deformation field, thereby creating a transformed joined model comprising a transformed reference object model and a transformed vessel model; and a registration step for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model.

In a further aspect of the invention, a computer program product to be loaded by a computer arrangement comprises instructions for registering a vessel model with an image data set based on a joined model comprising a reference object model and the vessel model, the computer arrangement comprising a processing unit and a memory, the computer program product, after being loaded, providing said processing unit with the capability to carry out the following tasks of:

placing the joined model in a space of the image data set, thereby creating a placed joined model comprising a placed reference object model and a placed vessel model;

computing a deformation field based on a landmark displacement field comprising displacements of landmarks of the placed reference object model relative to corresponding landmarks in the image data set;

transforming the placed joined model using the deformation field, thereby creating a transformed joined model comprising a transformed reference object model and a transformed vessel model; and registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model.

Modifications and variations of the image acquisition apparatus, of the workstation, of the method, and/or of the computer program product, which correspond to modifications of the system and variations, can be carried out by a skilled person on the basis of the present description.

The skilled person will appreciate that the method may be applied to volumetric, i.e. three-dimensional (3D) and four-dimensional (4D) image data acquired by various acquisition modalities such as, but not limited to, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

The same reference numerals are used to denote similar parts throughout the figures.

DETAILED DESCRIPTION OF EMBODIMENTS

Figure 1:
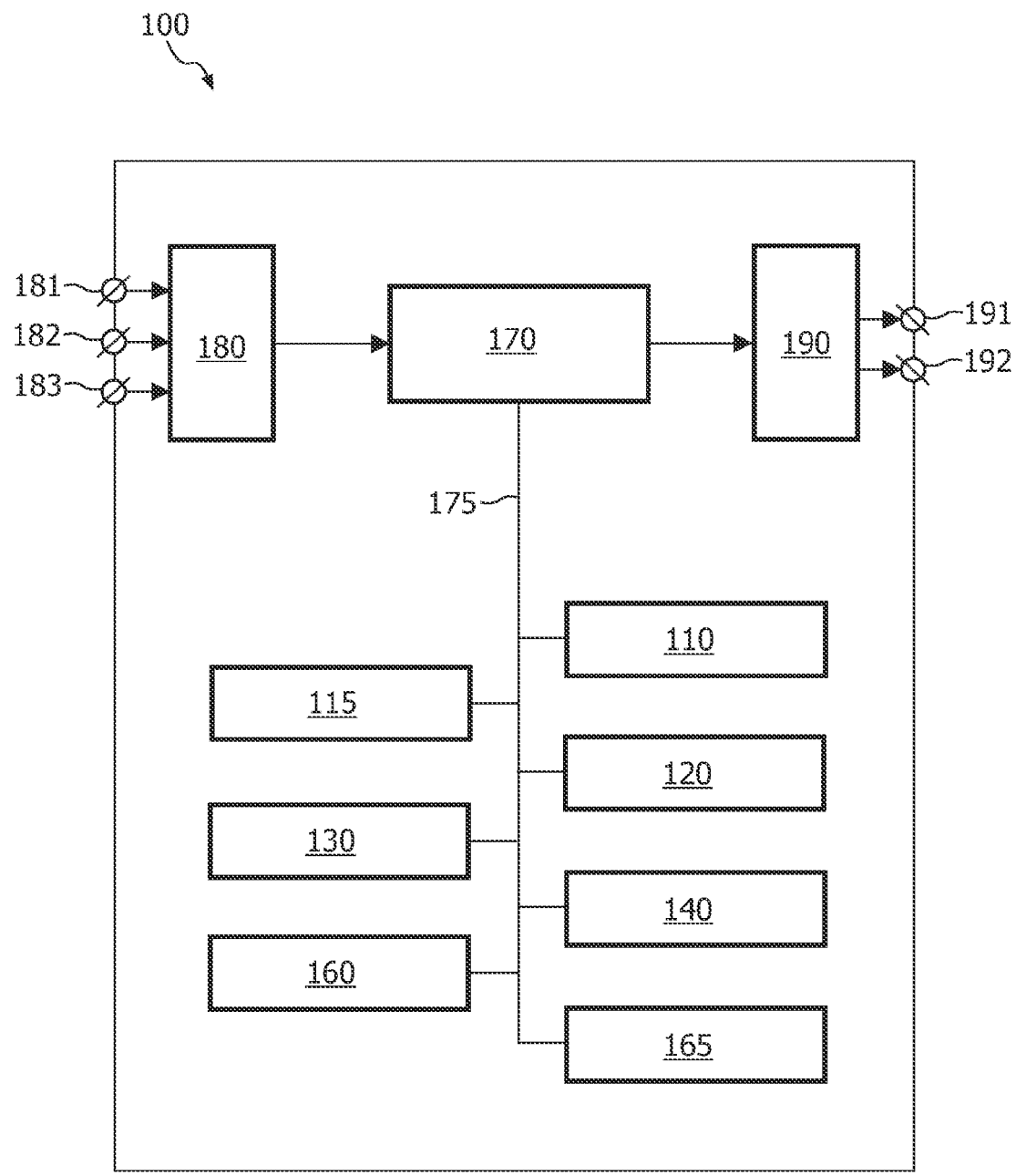
FIG. 1 schematically shows a block diagram of an exemplary embodiment of the system.

FIG. 1 schematically shows a block diagram of an exemplary embodiment of the system 100 for registering a vessel model with an image data set based on a joined model comprising a reference object model and the vessel model, the system comprising:

a placement unit 110 for placing the joined model in a space of the image data set, thereby creating a placed joined model comprising a placed reference object model and a placed vessel model;

a computation unit 120 for computing a deformation field based on a landmark displacement field comprising displacements of landmarks of the placed reference object model relative to corresponding landmarks in the image data set;

a transformation unit 130 for transforming the placed joined model using the deformation field, thereby creating a transformed joined model comprising a transformed reference object model and a transformed vessel model; and a registration unit 140 for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model.

The exemplary embodiment of the system 100 further comprises the following optional units:

an adaptation unit 115 for adapting the placed reference object model to the image data set;

a control unit 160 for controlling the workflow in the system 100;

a user interface 165 for communicating with a user of the system 100; and a memory unit 170 for storing data.

In an embodiment of the system 100, there are three input connectors 181, 182 and 183 for the incoming data. The first input connector 181 is arranged to receive data coming in from data storage such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to data storage such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows a quick access to relevant data portions by the units of the system 100. The input data may comprise, for example, an image data set and the joined model. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the registered vessel model and the transformed reference object model. The memory unit 170 is also arranged to receive data from and to deliver data to the units of the system 100 comprising the placement unit 110, the adaptation unit 115, the computation unit 120, the first transformation unit 130, the registration unit 140, the control unit 160, and the user interface 165 via a memory bus 175. The memory unit 170 is further arranged to make the output data available to external devices via any of the output connectors 191 and 192. Storing the data from the units of the system 100 in the memory unit 170 may advantageously improve the performance of the units of the system 100 as well as the rate of transfer of the output data from the units of the system 100 to external devices.

Alternatively, the system 100 may not comprise the memory unit 170 and the memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit 160 may be arranged to receive control data from and to provide control data to the units of the system 100. For example, after computing the deformation field the computation unit 120 may be arranged to send a control data "the deformation field is computed" to the control unit 160 and the control unit 160 may be arranged to provide a control data "transform the joined model using the deformation field" to the transformation unit 130 requesting the transformation unit 130 to transform the placed joined model. Optionally, a control function may be implemented in another unit of the system 100.

In an embodiment of the system 100, the system 100 comprises a user interface 165 for communicating with the user of the system 100. The user interface 165 may be arranged to provide the user with means for manually placing the joined model in the image data space. Optionally, the user interface may receive a user input for selecting a mode of operation of the system 100 such as a mode for selecting a joined model and/or for selecting an adaptation method to be used by the adaptation unit 115. The skilled person will understand that more functions may be advantageously implemented in the user interface 165 of the system 100.

A volumetric, i.e. three-dimensional (3D), image data set comprises data elements. Each data element (x, y, z, I) of the image data comprises a location (x, y, z), typically represented by three Cartesian coordinates x, y, z in an image data space coordinate system, and an intensity I at this location. An image data element may also be represented by a voxel, a small, typically cubic or cuboidal, volume and intensity assigned to this volume. The coordinates x, y, z may be coordinates of a vertex of a cubic or cuboidal voxel. The space of the image data set, also referred to as the image data space or the image data volume, may be defined as a volume comprising all locations (x, y, z) comprised in the image data elements (x, y, z, I). Also, the image volume may be interpreted as a union of all voxel volumes. The volumetric image data set may be organized as a collection of substantially planar sections or slices of the image volume, e.g. sections or slices substantially perpendicular to a z axis of the coordinate system. A 4D image data set comprises a collection of volumetric image data sets acquired at different time instances or at different phases of motion.

The system 100 is especially useful when applied to a coronary artery, e.g. to the right coronary artery (RCA) or to the main coronary artery tree comprising the RCA, the left anterior descending (LAD) coronary artery and the circumflex (LCX) artery, as a vessel and to the heart at a phase of the cardiac cycle, e.g. at the end-diastolic phase, as a reference object. However, the skilled person will appreciate that the system 100 may be used for registering any vessel-like, i.e. tubular, structure such as, but not limited to, a blood vessel, an air pipe and a nerve. The reference object may be any anatomical structure which is useful in determining relative localization of the vessel-like structure such as, but not limited to, a rib, a vertebrae and a kidney. Preferably, the reference object comprised in the image data set is easily detectable and can be delineated relatively easily using a reference object model. The term "localization" used with reference to a vessel or to a vessel model describes the whole vessel or vessel model, respectively, including the position, orientation and configuration of the whole vessel or vessel model.

An exemplary joined model comprising a multi-surface cardiac model of four cardiac chambers, and main artery and vein trunks is described in an article by J. von Berg and C. Lorenz entitled "Multi-surface Cardiac Modeling, Segmentation, and Tracking" in A. F. Frangi et al. (Eds.): FIMH 2005, LNCS 3504, Springer-Verlag Berlin Heidelberg 2005, pages 1-11, hereinafter referred to as Ref. 3. Nowadays, the object models are often mean models, i.e. the models are constructed based on a plurality of objects, e.g. the hearts from a plurality of patients. Such mean models describe typical features of the modeled object. The multi-surface cardiac model described in Ref. 3 is such a mean model, wherein the cardiac surfaces are described using triangular meshes. Other meshes, e.g. simplex meshes, may also be used.

Modeling coronary arteries is described in an article by C. Lorenz et al entitled "Modeling the coronary artery tree" in International Conference on Shape Modeling and Applications 2004 (SMI'04) 2004, Genoa, Italy, Jun. 6-9, 2004, pages 354-357. The paper uses a tree model of the coronary artery centerlines represented as points, also referred to as control points, connected by line segments. Alternatively, the control points can be connected by, for example, cubic splines, B-splines or Bezier curves. The skilled person will understand that the scope of the claims does not depend on the implementation of a vessel centerline. A joined model of cardiac and vascular structures is described in an article by C. Lorenz and J. von Berg entitled "Towards a Comprehensive Geometric Model of the Heart" in A. F. Frangi et al (Eds.), FIMH 2005, LNCS 3504, Springer Verlag, Berlin, Germany, 2005, pages 102-112, hereinafter referred to as Ref. 4.

The placement unit 110 of the system 100 is arranged for placing the joined model in a space of the image data set. The placement may be done automatically and may be based on detecting the reference object using, for example, ray casting described in an article by C. Lorenz and J. von Berg entitled "Fast automated object detection by recursive casting of search rays" in Proc. CARS. 2005, pages 230-235, or a Hough transform described in an article by H. Schramm et al entitled "Towards Fully Automatic Object Detection and Segmentation" in Proc. SPIE Vol. 6144, 614402, Medical Imaging 2006: Image Processing, J. M. Reinhardt and J. P. Pluim (Eds.), pages 11-20. Optionally, the placement may be refined or performed manually using means for manipulating a model provided by the user interface 165. The placement is carried out using rigid transformations. Optionally, the placement may involve a further global transformation, e.g. scaling, of the joined model.

The computation unit 120 is arranged for computing a dense deformation field based on a landmark displacement field comprising displacements of landmarks of the placed reference object model relative to corresponding landmarks in the image data set. The set of landmarks may be comprised in the joined model as described in Ref. 4. The system may also obtain a user input for determining locations of the corresponding landmarks in the image data set. Alternatively, locations of the corresponding landmarks in the image data set may be computed by the system using landmark feature detection, for example. When locations of the landmarks of the placed reference object model and locations of the corresponding landmarks in the image data set are determined, the computation unit 120 is arranged to compute the landmark displacement field comprising displacements, i.e. vectors of displacements, of landmarks of the placed reference object model relative to the corresponding landmarks in the image data set. This field is further used by the computation unit 120 for computing a dense deformation field. For example, the computation unit 120 may be arranged to interpolate the displacement field using thin-plate splines. Constructing a dense vector field using the thin-plate-spline interpolation of a sparse vector field is described in an article by F. L. Bookstein entitled "Principal warps: Thin-plate splines and the decomposition of deformations" in IEEE Transactions on Pattern Analysis and Machine Intelligence, Vol. 11, pages 567-585, 1989. The word "dense" is used here in the sense that the deformation field can be applied to the image data set space to transform the placed joined model.

In an embodiment of the system 100, the system further comprises an adaptation unit 115 for adapting the placed reference object model to the image data set, thereby defining the corresponding landmarks in the image data set as the landmarks of the adapted placed reference object model. The adaptation unit 115 allows the corresponding landmarks to be identified automatically using, for example, a method described in an article by O. Ecabert et al entitled "Towards Automatic Full Heart Segmentation in Computed-Tomography Images" 32th Conference on Computers in Cardiology, 2005, pages 223-226. Alternatively, the adaptation method employed by the adaptation unit 115 may be semi-automatic or manual.

In an embodiment of the system 100 the reference object model comprises a mesh. The mesh may be a polygonal mesh, e.g. a triangular mesh. Advantageously, the set landmarks may be a subset of vertices of a placed mesh of the placed reference object model. For example, all vertices of the placed mesh may be landmarks of the reference object model. Optionally, only vertices corresponding to "strong" image data set features detected during the adaptation of the placed mesh to the image data set, e.g. vertices with computed weights (for the definition of weights see section 2.2 of the article by J. Weese et al entitled "Shape constrained deformable models for 3D medical image segmentation" in Proc. IPMI. 2001, pages 380-387) greater than a threshold, may be used to define the landmarks of the placed reference object model. The vertices of the adapted placed mesh may then be used as the corresponding landmarks in the image data set.

The deformation field is used by the transformation unit 130 to transform the placed joined model into a transformed joined model by applying the deformation field to the placed joined model. This deformation field transforms both the placed reference object model and the placed vessel model. Since the deformation field is constructed by registering the landmarks of the placed reference object model with the corresponding landmarks in the image data set, the transformation of the reference object model is satisfactory for delineating the reference object in the image data set. However, the localization of the transformed vessel model may be a rather crude estimate of an actual vessel localization, useful as a starting localization for further registration of the transformed vessel model.

The registration unit 140 of the system 100 is arranged for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model. Optimizing an objective function may be based on finding a maximum or a minimum of the objective function, for example. Parameters for describing the vessel model may comprise coordinates of control points of the vessel centerline. The vessel centerline may be interpolated using B-splines. During registration, each control point may vary its coordinates in a plane substantially orthogonal to the tangent of the B-spline at the control point or within a sphere centered at the original control point, for example. The orientation of the plane or the sphere may be adjusted when the vessel centerline deforms.

In an embodiment of the system 100 the location-prior term may penalize displacement of the centerline in the modified transformed vessel model from its location in the transformed vessel model. This can be realized using a distance transformation described, for example, by G. Borgefors in an article entitled "Distance transforms in digital images" in IEEE Transactions on Pattern Analysis and Machine Intelligence, Vol. 34, 1986, pages 344-371. The distance transformation is defined as the distance from a location in the image data space to a certain set of locations in the image data space. The distance from a location in the image data space to the certain set of locations may be the Euclidean distance of said location to the closest location comprised in the certain set of locations. The certain set of locations may describe a typical, i.e. most likely, localization of the vessel. The reciprocal of the distance from a location in the image data space to the set of locations describing a typical localization of the vessel may be interpreted as likelihood that the vessel is located at said location in the image data space.

The certain set of locations describing a typical localization of the vessel may be defined in many ways. For example, the certain set of locations may be defined by locations on the vessel centerline, e.g. defined by voxels intersected by the vessel centerline. Optionally, the certain set of locations may further comprise locations adjacent to the locations on the vessel centerline or within certain distance from the centerline. Another possibility is to identify localization of each of the sample vessel models from a population of sample vessel models used for constructing a mean vessel model. Each sample vessel model may be placed in the image data space and transformed by the transformation unit 130 using the deformation field computed by the computation unit 120. All locations of the transformed sample vessel models define the certain set of locations. The skilled person will appreciate that other ways of defining the certain set of locations may be useful and that the scope of the claims does not depend on the definition of the certain set of locations.

In an embodiment of the system 100, the location-prior term may penalize displacement of the centerline in the modified transformed vessel model relative to the transformed reference object model. For example, a subset of the corresponding landmarks in the image data set, identical with a subset of landmarks comprised in the adapted placed reference object model may be used as a reference set. For each pair of subsequent control points along the centerline, the area of a triangle defined by the pair of control points and a location of a landmark from the reference set may be computed. Optionally, the set of control points may be replaced by another, e.g. larger, set of points along the centerline. The areas of triangles defined by all pairs of the control points may be summed up. The sum can be compared to a "ground truth" sum learned, for example, using a plurality of training image data sets. Similar sums can be computed for the remaining landmarks. The location-prior term may be defined as an exponential function of the sums computed for each landmark from the reference set. For example, the exponent may be a negative square root of the weighted sum of squares of differences of the computed sum and the "ground truth" sum. The weights are non-negative.

The skilled person will appreciate that other location-prior terms may also be used and that the described location-prior terms illustrate the invention rather than limit the scope of the claims.

In an embodiment of the system 100, the objective function further comprises a vesselness term for detecting a vessel in the image data set. An exemplary vesselness term uses vesselness filters for detecting bright elongated structures of a certain diameter. Vesselness filters are described in Ref. 2. A vesselness filter applied to a filter location in the image data space yields a measure of vesselness at the filter location, i.e. likelihood of a vessel being at the filter location. The vesselness filter has a scale parameter which corresponds to the diameter of the detected vessel. The measure of vesselness depends on the value of the scale parameter. If the modified transformed vessel model comprises an expected diameter of the vessel at the filter location then this expected diameter can be compared to the value of the scale parameter at which the measure of vesselness attains a maximum. The closer the expected vessel diameter to the scale parameter at which the measure of vesselness attains a maximum, the higher the likelihood of the vessel being at the filter location. Alternatively, the scale of the vesselness filter may be set to the expected vessel diameter. A vesselness filter also estimates the tangential of a vessel-like structure at the filter location. This additional information may be compared to an expected orientation of the vessel defined by the modified transformed vessel model using a dot product of the tangential of a vessel-like structure by the expected direction of the vessel defined by the modified transformed vessel model, for example.

In an embodiment, the vesselness term and the location-prior term are combined and the objective function external energy term can be written as $E_{ext} = \Sigma_j C(s_j, \sigma_j)$ where $C(s_j, \sigma_j) = d(s_j) w(s_j, \sigma_j) D(s_j) + I(s_j)$ for each filter location $s_j$, e.g. each control point of the centerline of the modified transformed vessel model, in the image data space. Here $\sigma_j$ is the scale of the vesselness filter equal to the expected vessel diameter comprised in the vessel model; $d(s_j)$ is the dot product of the normalized tangential of a vessel-like structure at a filter location $s_j$ by the expected direction of the vessel defined by the modified transformed vessel model at this location; $D(s_j)$ is the reciprocal distance from the filter location $s_j$ to the certain set of locations; and $w(s_j, \sigma_j)$ is the vesselness measure at the filter location $s_j$. The vesselness measure $w(s_j, \sigma_j)$ may be one of the filters described in Ref. 2, in C. Lorenz et al "A multi-scale line filter with automatic scale selection based on the Hessian matrix for medical image segmentation", Lecture Notes In Computer Science, Vol. 1252, Proceedings of the First International Conference on Scale-Space Theory in Computer Vision, 1997, pages, 152-163, in Y. Sato et al "3D multiscale line filter for segmentation and visualization of curvilinear structures in medical images", Conference on Computer Vision, Virtual Reality and Robotics in Medicine and Medial Robotics and Computer-Assisted Surgery, 1997, pages 213-222, or a weighted sum of all of them. An optional term $I(s_j)$ evaluates image data intensity at the filter location $s_j$. This term may be used, for example, to differentiate between a pulmonary vessel and a coronary artery. In a CT image data set, a pulmonary vessel may show a similar vesselness measure to a coronary artery, but the coronary artery is much brighter.

In an embodiment, the external energy term can be written as $E_{ext} = E_{vess} + E_{loc}$ where $E_{vess} = \Sigma_j (d(s_j) w(s_j, \sigma_j) + I(s_j))$ is a vesselness term and $E_{loc} = \Sigma_j D(s_j)$ is a location-prior term. The skilled person will know other ways of constructing an external energy term. The implementations described illustrate the embodiments and do not limit the scope of the claims.

The objective function may further comprise an internal energy term which penalizes high curvatures of the centerline. Optionally, the total length of the centerline can serve as a global measure of curvature, because curved centerlines tend to be longer than straight centerlines.

The skilled person will understand that there are many other useful terms which can be included in the objective function. These terms comprise, but are not limited to, features learned from training images using a method described in J. Peters et al, "Feature optimization via simulated search for model-based heart segmentation", CARS 2005—Computer Assisted Radiology and Surgery, Proceedings of the 19th International Congress and Exhibition Berlin, Germany, Jun. 22-25, 2005; deviation from a mean vessel model shape; location relative to a further reference object adapted to the image data set; and bending and stretching energy terms. The scope of the claims does not depend on the inclusion of these terms.

The skilled person will further understand that other ways of optimizing an objective function are possible. For example, one can redefine an objective function in such a way that optimizing the objective function is based on finding a minimum of the objective function. Optionally, one can define a multi-dimensional objective function yielding a plurality of values. The parameters of the optimized objective function, e.g. the control points of the modified transformed vessel model centerline, which correspond to an optimum of the objective function, define the vessel model registered with the image data set.

The skilled person will understand that other embodiments of the system 100 are also possible. It is possible, among other things, to redefine the units of the system and to redistribute their functions. For example, in an embodiment of the system 100, the functions of the placement unit 110 and of the adaptation unit 115 may be combined to one initialization unit. In a further embodiment of the system 100, there can be a plurality of term computation units. Each unit may be arranged to compute a term of the objective function. The user may define the objective functions by providing an input for selecting term computation units to be employed by the registration unit 140 for computing the objective function.

The units of the system 100 may be implemented using a processor. Normally, their functions are performed under the control of a software program product. During execution, the software program product is normally loaded into a memory, like a RAM, and executed from there. The program may be loaded from a background memory, like a ROM, hard disk, or magnetic and/or optical storage, or may be loaded via a network like Internet. Optionally, an application-specific integrated circuit may provide the described functionality.

Figure 2:
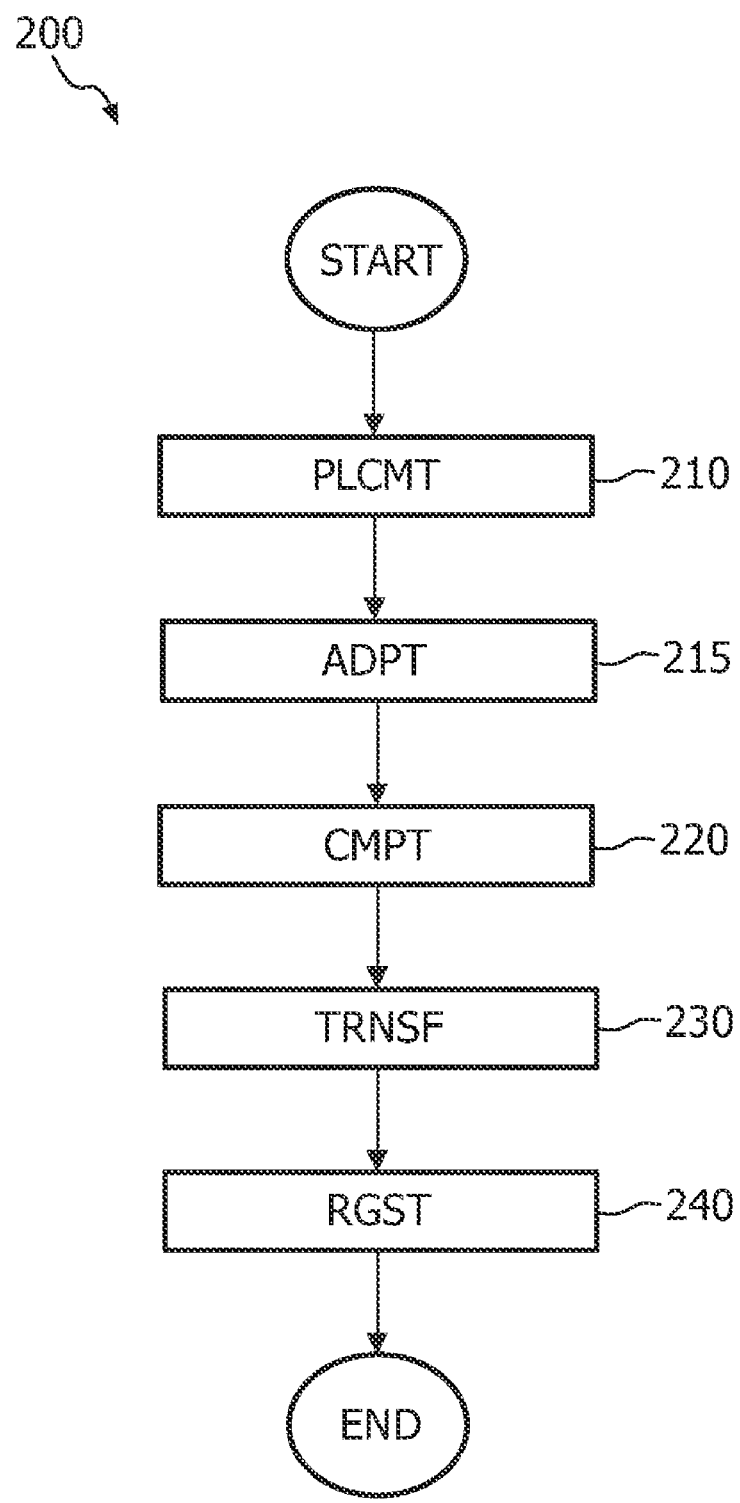
FIG. 2 shows a flowchart of an exemplary implementation of the method.

FIG. 2 shows a flowchart of an exemplary implementation of the method 200 of registering a vessel model with an image data set based on a joined model comprising a reference object model and the vessel model. The method 200 begins with a placement step 210 for placing the joined model in a space of the image data set, thereby creating a placed joined model comprising a placed reference object model and a placed vessel model. After the placement step 210 the method 200 continues to an adaptation step 215 for adapting the placed reference object model to the image data set, thereby defining the corresponding landmarks in the image data set. After the adaptation step 215 the method 200 continues to a computation step 220 for computing a deformation field based on a landmark displacement field comprising displacements of landmarks of the placed reference object model relative to corresponding landmarks in the image data set. After the computation step 220 the method 200 continues to a transformation step 230 for transforming the placed joined model using the deformation field, thereby creating a transformed joined model comprising a transformed reference object model and a transformed vessel model. After the transformation step 230 the method 200 continues to a registration step 240 for registering the transformed vessel model with the image data set based on modifying the transformed vessel model and optimizing an objective function of the modified transformed vessel model, wherein the objective function comprises a location-prior term based on a localization of the modified transformed vessel model relative to the transformed joined model. After the registration step 240 the method terminates.

The skilled person may change the order of some tasks defined in the steps of the method 200 or perform some tasks concurrently using threading models, multi-processor systems or multiple processes without departing from the concept as intended by the present invention. Optionally, two or more steps of the method 200 of the current invention may be combined to one step. Optionally, a step of the method 200 of the current invention may be split into a plurality of steps.

Figure 3:
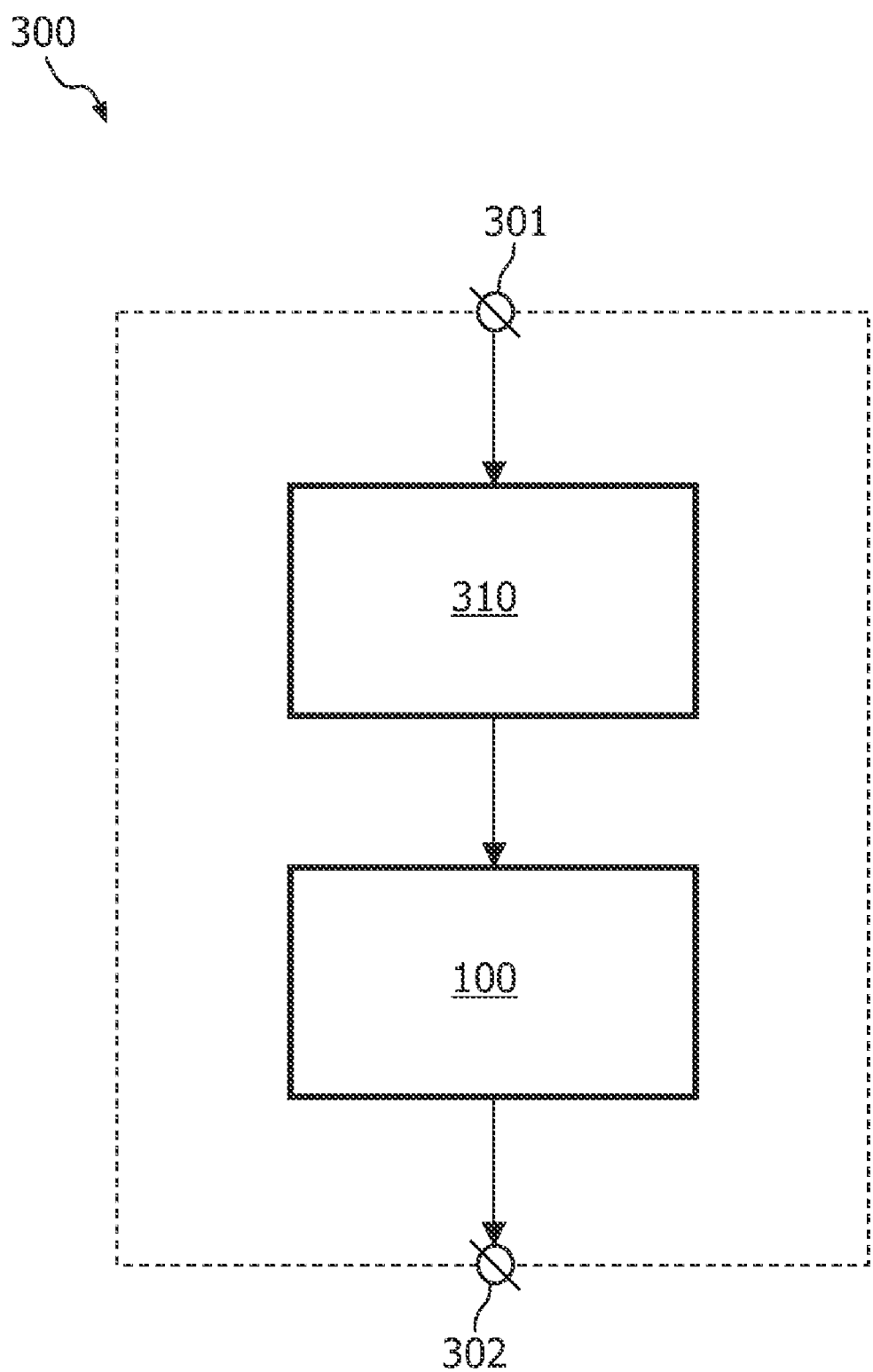
FIG. 3 schematically shows an exemplary embodiment of the image acquisition apparatus.

FIG. 3 schematically shows an exemplary embodiment of the image acquisition apparatus 300 employing the system 100, said image acquisition apparatus 300 comprising an image acquisition unit 310 connected via an internal connection with the system 100, an input connector 301, and an output connector 302. This arrangement advantageously increases the capabilities of the image acquisition apparatus 300 providing said image acquisition apparatus 300 with advantageous capabilities of the system 100 for registering a vessel model with an image data set based on a joined model comprising a reference object model and the vessel model. Examples of image acquisition apparatus comprise, but are not limited to, a CT system, an X-ray system, an MRI system, a US system, a PET system, a SPECT system, and an NM system.

Figure 4:
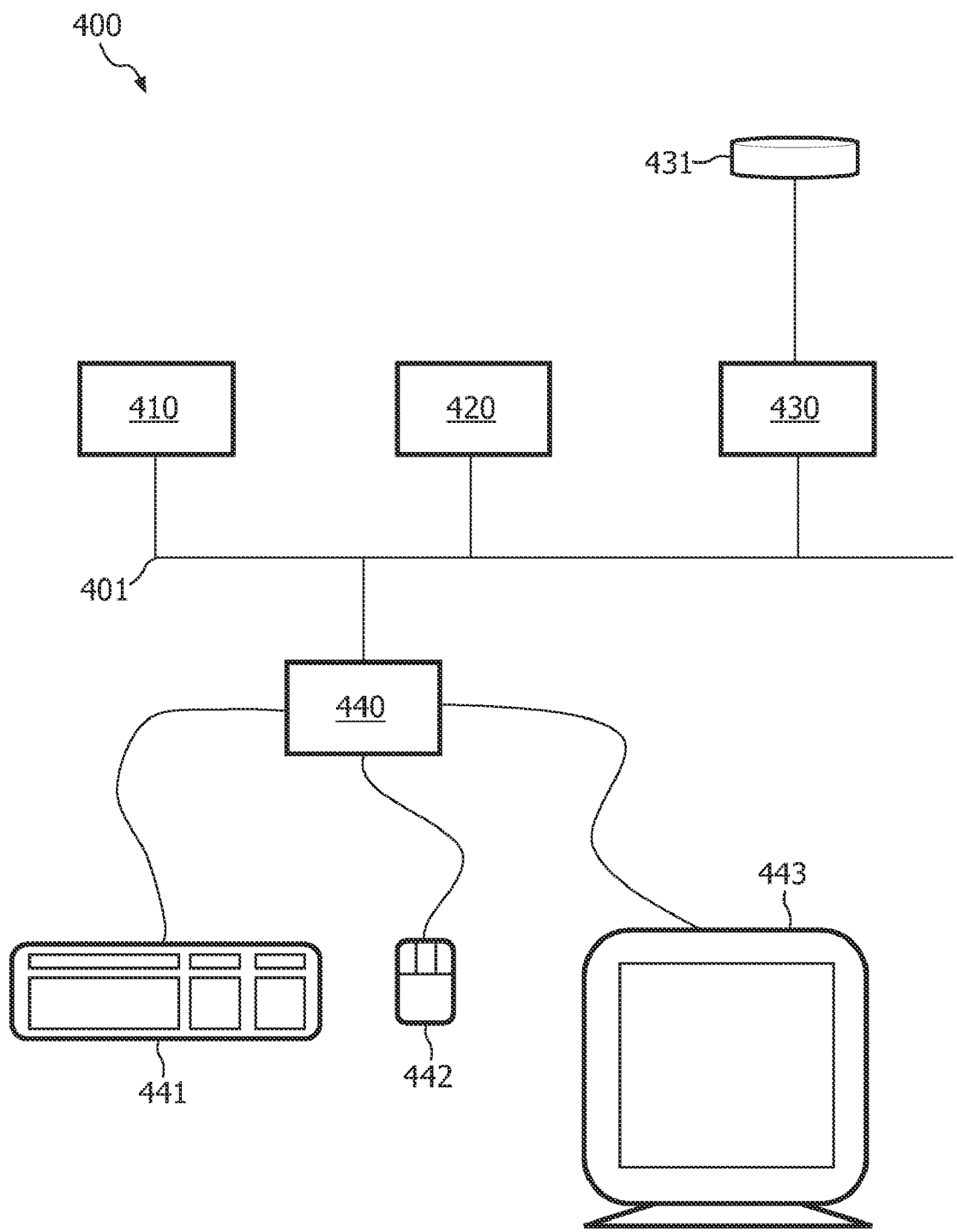
FIG. 4 schematically shows an exemplary embodiment of the workstation.

FIG. 4 schematically shows an exemplary embodiment of the workstation 400. The workstation comprises a system bus 401. A processor 410, a memory 420, a disk input/output (I/O) adapter 430, and a user interface (UI) 440 are operatively connected to the system bus 401. A disk storage device 431 is operatively coupled to the disk I/O adapter 430. A keyboard 441, a mouse 442, and a display 443 are operatively coupled to the UI 440. The system 100 of the invention, implemented as a computer program, is stored in the disk storage device 431. The workstation 400 is arranged to load the program and input data into memory 420 and execute the program on the processor 410. The user can input information to the workstation 400 using the keyboard 441 and/or the mouse 442. The workstation is arranged to output information to the display device 443 and/or to the disk 431. The skilled person will understand that there are numerous other embodiments of the workstation 400 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The use of the words first, second and third, et cetera does not indicate any ordering. These words are to be interpreted as names.

The invention claimed is:

1. A system for registering a vessel model with an image data set based on a joined model comprising a reference object model and the vessel model, the system comprising:
   a placement unit for placing the joined model in a space of the image data set, thereby creating a placed joined model comprising a placed reference object model and a placed vessel model;
   a computation unit for computing a deformation field based on a landmark displacement field comprising displacements of landmarks of the placed reference object model relative to corresponding landmarks in the image data set;
   a transformation unit for transforming the placed joined model using the deformation field, thereby creating a transformed joined model comprising a transformed reference object model and a transformed vessel model; and
   a registration unit for registering the transformed vessel model with the image data set based on modifying the transformed vessel model and optimizing an objective function of the modified transformed vessel model,
   wherein the objective function comprises a location-prior term based on a localization of the modified transformed vessel model relative to the transformed joined model.

2. A system as claimed in claim 1 further comprising an adaptation unit for adapting the placed reference object model to the image data set, thereby defining the corresponding landmarks in the image data set.

3. A system as claimed in claim 2, wherein the reference object model comprises a mesh comprising a plurality of vertices.

4. A system as claimed in claim 1, wherein the vessel model comprises a plurality of control points for describing a vessel centerline.

5. A system as claimed in claim 1, wherein the objective function further comprises a vesselness term based on a vesselness filter for computing a measure of vesselness at a location of the vesselness filter in the space of the image data set.

6. A system as claimed in claim 5, wherein the vessel model further comprises a plurality of diameters of the vessel for describing a vessel wall.

7. A system as claimed in claim 1, wherein the location-prior term depends on the transformed reference object model.

8. An image acquisition apparatus comprising the system as claimed in claim 1.

9. A workstation comprising the system as claimed in claim 1.

10. A method of registering a vessel model with an image data set based on a joined model comprising a reference object model and the vessel model, the method comprising:
    a placement step for placing the joined model in a space of the image data set, thereby creating a placed joined model comprising a placed reference object model and a placed vessel model;
    a computation step for computing a deformation field based on a landmark displacement field comprising displacements of landmarks of the placed reference object model relative to corresponding landmarks in the image data set;
    a transformation step for transforming the placed joined model using the deformation field, thereby creating a transformed joined model comprising a transformed reference object model and a transformed vessel model; and
    a registration step for registering the transformed vessel model with the image data set based on modifying the transformed vessel model and optimizing an objective function of the modified transformed vessel model,
    wherein the objective function comprises a location-prior term based on a localization of the modified transformed vessel model relative to the transformed joined model.

11. A computer program product, stored on a non-transitory computer readable medium, to be loaded by a computer arrangement, comprising instructions for registering a vessel model with an image data set based on a joined model comprising a reference object model and the vessel model, the computer arrangement comprising a processing unit and a memory, the computer program product, after being loaded, providing said processing unit with the capability to carry out the tasks of:
    placing the joined model in a space of the image data set, thereby creating a placed joined model comprising a placed reference object model and a placed vessel model;
    computing a deformation field based on a landmark displacement field comprising displacements of landmarks of the placed reference object model relative to corresponding landmarks in the image data set;
    transforming the placed joined model using the deformation field, thereby creating a transformed joined model comprising a transformed reference object model and a transformed vessel model; and
    registering the transformed vessel model with the image data set based on modifying the transformed vessel model and optimizing an objective function of the modified transformed vessel model,
    wherein the objective function comprises a location-prior term based on a localization of the modified transformed vessel model relative to the transformed joined model.

* * * * *